United States Patent [19]

Frayman

[11] Patent Number: 5,554,109
[45] Date of Patent: Sep. 10, 1996

[54] COMPACTLY ASSEMBLED TAMPON APPLICATOR

[76] Inventor: Max Frayman, 25 Quinnehtuk Cir., Longmeadow, Mass. 01106

[21] Appl. No.: 370,192

[22] Filed: Jan. 9, 1995

[51] Int. Cl.⁶ .................................................. A01F 13/32
[52] U.S. Cl. ............................................ 604/15; 604/18
[58] Field of Search ................................. 604/11, 14, 15, 604/16, 18

[56] References Cited

U.S. PATENT DOCUMENTS

| | | | |
|---|---|---|---|
| 3,575,169 | 4/1971 | Voss et al. | 604/18 |
| 3,696,812 | 10/1972 | Jaycox | 604/18 |
| 3,699,962 | 10/1972 | Hanke | 604/18 |
| 4,271,835 | 6/1981 | Conn et al. | 604/15 |
| 4,286,596 | 9/1981 | Ring | 604/16 |
| 4,479,791 | 10/1984 | Sprague | 604/18 |
| 4,846,802 | 7/1989 | Sanders, III | 604/15 |
| 4,911,687 | 3/1990 | Stewart et al. | 604/15 |
| 4,960,417 | 10/1990 | Tarr, Jr. et al. | 604/15 |
| 5,330,421 | 7/1994 | Tarr et al. | 604/16 |

Primary Examiner—Paul J. Hirsch

[57] ABSTRACT

A tampon applicator assembly of compact type is provided comprising an outer tube, an inner tube slidably nested therein and a tampon stored inside of the inner tube. A small portion of the tampon protruding from a proximal end of the inner tube. The inner tube has to be partially withdrawn from the outer tube in the distal direction until the proximal end of the inner tube will be placed behind the distal end of the tampon. To prevent distal movement of the tampon relative to the outer tube during the partial withdrawal the outer tube comprises a holding means. The holding means comprises at least one set of circumferentially located stiff cogs fixed to the inner surface of the outer tube. Each cog has at least one biting edge pressed against the side surface of the protruding portion of the tampon when the applicator is completely assembled.

12 Claims, 1 Drawing Sheet

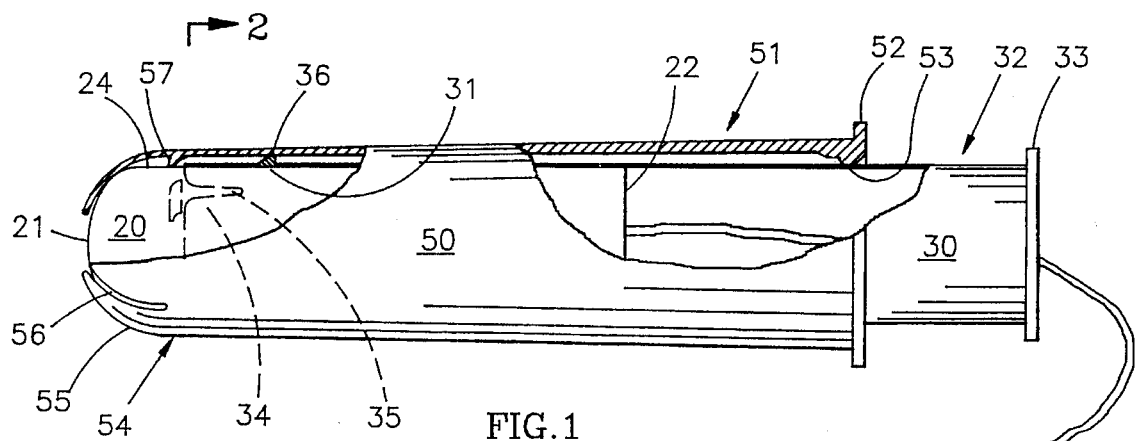
FIG. 1
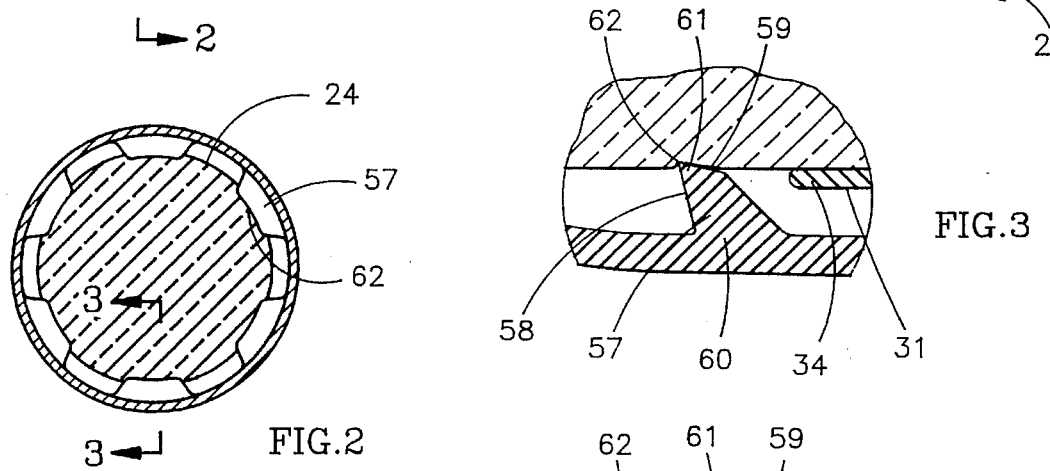
FIG. 2
FIG. 3
FIG. 2A
FIG. 4
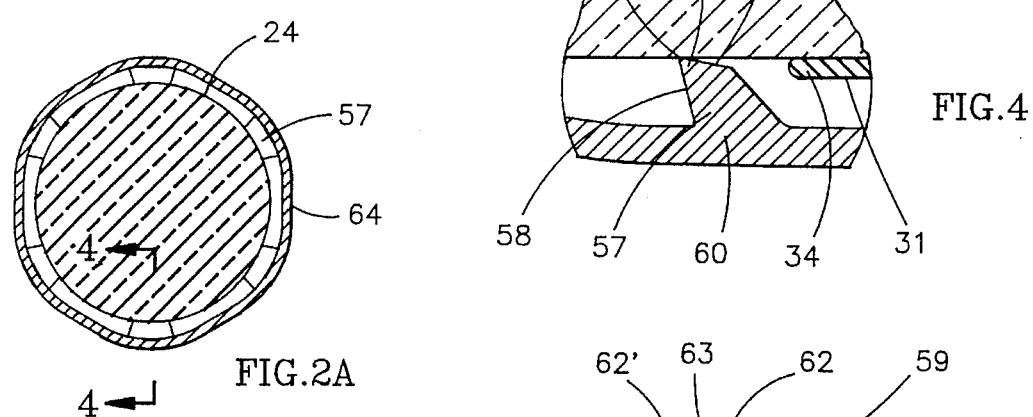
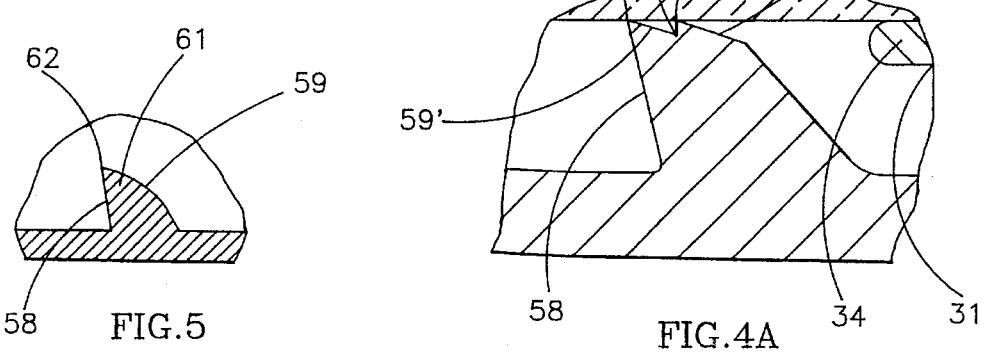
FIG. 5
FIG. 4A

COMPACTLY ASSEMBLED TAMPON APPLICATOR

BACKGROUND OF THE INVENTION

The present invention relates to a tampon insertion device and, more particularly, to a preferably short and compact type.

The tampon applicator assembly consists of an outer tube (the insertion tube or barrel)having a forward end (leading end or insertion end, or distal discharge end), a tampon positionable within the outer tube immediately inward of its leading end, and an inner tube (ejection tube or plunger, or pusher, or ejector) telescopically receivable within the outer tube rearwardly of the tampon and functioning as the pusher for effecting the forward delivery of the tampon through the leading end of the outer tube.

As known, the tampon applicator is introduce vaginally and, subsequent to the forward delivery of the tampon, is withdrawable.

Tampon applicators are commonly of two types, distinguished from each other by their length.

Conventional type applicators are usually of the ready-for-use type whereas compact type applicators have to be prepared for use by the user.

In the conventional type applicator, the tampon is located inside the leading potion of the outer rube, and the inner tube or the pusher is located within the outer tube rearwardly of the tampon.

In the compact type applicator, the tampon (or at least the greater portion thereof) is located within the inner tube. In operational use, the user has to hold the rear end of the outer tube by the fingers of one hand and grip the rear end of the inner tube to retract it by the fingers of the other hand so that front end of the inner tube will be behind rear end of the tampon.

The length of the outer tube of all types of applicators desirably should be approximately 2¾" in order to satisfy the necessity of placing the tampon to depth approximately 2" to rear end of the tampon and to have a gripping area approximately ¾" in length.

The rear part of the inner tube will extend from the rear open end of the outer tube approximately 2" so as to give possibility for a full expulsion of the tampon through leading end of the outer tube. For this reason, the conventional type applicator has a full length of approximately 4¾.

Contrariwise, in the compact type applicator, the rear part of the inner tube extends from the rear open end of the outer tube between ⅜" to ⅝". The overall length of the assembled applicator is approximately 3¼".

Any attempt to fabricate an applicator significantly shorter will lead to at least one salient disadvantage: a wrong location of the tampon in the catamenial canal, or a minimized convinience of the gripping of the rearward end of the inner tube for its retraction or an increased overall diameter of the applicator.

To facilitate inner tube retraction, any compact applicator has to comprise a tampon holding means associated with the outer tube for engaging a tampon carried in the inner tube so as to resist rearward movement of the tampon, while permit its forward movement through the discharge end of the outer tube during expelling of the tampon into the body cavity.

Lately it has been introduced a lot of structural solution of the tampon holding means, which can be divided into three major groups.

First group includes the applicators which comprise an additional part, such as the inner sleeve located between inner and outer tubes shown in U.S. Pat. No 4,676,773. The necessity to fabricate an additional part and the using of more complicated assembling machinery disadvantageously increase the cost of production of such tampon applicators. Besides, the tampon applicator according to U.S. Pat. No 4,676,773 suffers disadvantage from the user's safety standpoint. Very often the rear end of a tampon has an unbound particle, which, in this particular applicator structure, can be tangled between ring 12 and folded flange 11(see FIG. 11 of U.S. Pat. No 4,676,773). If this happened, the outer tube will be withdrawn alone. The withdrawal of the remaining parts of the applicator can necessitate emergency medical assistance.

Second group includes the applicators, in which tampon holding means comprises at least one projection, fixed to inner surface of outer tube, extending inwardly through a longitudinal window in the inner tube and located rearwardly of rear end of the tampon. Such applicators are described in U.S. Pat. Nos 4,276,881; 4,286,595; 4,291,596; 4,891,042. All applicators of this group suffer from the same disadvantage following from necessity of additional rotational orientation of the tubes prior to the assemblage of the applicator.

Third group includes the applicators in which tampon holding means located adjacent of the discharge end of the outer tube and coacts with the front end of the tampon. The applicator described in U.S. Pat. No 4,479,791 has a tampon completely stored in the inner space of the inner tube and tampon holding means in the form of thin elongated projections extending from inner surface of the outer tube inwardly through the openings between long fingers of the inner tube. Because of such structure, this applicator suffers the same disadvantage as the second group of applicators. Another disadvantage follows from a weakness of narrow long fingers of the inner tube. Sometimes they are not able to transfer to the tampon a longitudinal force applied to the rear end of the inner tube during expelling of the tampon. If they are bent and smashed, the tampon will be positioned improperly. Besides, if the tampon is highly compressed, those projections can be bent in the circumferential direction during the assembly of the applicator. In this case, the projections loose ability to hold tampon during partial withdrawal of the inner tube and such applicator cannot be used.

Each of the above listed patents is assigned to one of the major tampon manufacturers, but none of those tampon applicators had been commercially successful so far.

At the present time only one compact tampon applicator is commercially available, and it is fabricated in accordance with U.S. Pat. No 4,726,805 (used hereby as a reference). This patent describes an applicator with a tampon holding means comprising a set of flaps located circumferentially closely adjacent to the bases of the petals defining the leading end of the outer tube. Each flap is a thin circumferentially extended projection flexible in axial direction.

The flaps cannot sufficiently hold the portion of the tampon extending from the inner tube, if the tampon fabricated of straight cylindrical configuration. To increase tampon holding effect the extended portion made in form of a head, enlarged in diameter and positioned in front of the flaps.

Actually, many of these tampons have misalignment of the head and the remaining portion. Such tampons have the shoulder behind the head on one side and do not have it on the diametrally opposed side. Functional reliability of the applicator assembled with such tampon decreases, especially if a user uses applicator in environment existing in a public toilet.

So, this applicator necessitates the use of more complicated tampon making machinery, but does not provide reliable enough tampon applicator assembly.

SUMMARY OF THE INVENTION

Accordingly, it is an object of this invention to provide a compact tampon applicator assembly that eliminates the above described difficulties and disadvantages.

More particularly, it is an object of this invention to provide a compact tampon applicator assembly with highly reliable tampon holding means and, accordingly, to increase credence to compact type applicator as such.

Another object of this invention is to provide a compact tampon applicator assembly which prevents any disturbances of the sensitive tissue of the vagina during insertion and withdrawal of the applicator.

Another object of this invention is to provide a compact tampon applicator assembly comprising components which can be easily fabricated by existing high speed production machinery.

It is further object of this invention to provide a compact tampon applicator, comprising highly reliable tampon holding means, which can be easily assembled without rotational orientation of the tubes.

Lastly, it is object of this invention to provide a compact tampon applicator which satisfies certain environmental requirements by decreasing of bulk of wrapping and packaging materials and eliminating unrecyclable spoilages and rejects.

The foregoing and other objects of the invention are realized by a tampon applicator assembly provided with a tampon holding means, which comprises a set of circumferentially located stiff cogs rigidly fixed to the inner surface of the outer tube adjacent of bases of petals defining leading discharge end. This holding means prevents movement of the tampon in the rearward direction very efficiently and yet also allows easy passage of the tampon in the forward direction, when the latter has to be expelled. The holding means according to present invention can function properly and efficiently with the tampon having simple configuration and any compression accepted in the industry.

Other features and advantages of the present invention will become apparent from the following description of the invention which refers to the accompanying drawings.

BRIEF DESCRIPTION OF THE DRAWINGS

FIG. 1 is a partially sectioned longitudinal view of a tampon applicator according to present invention in the assembled position.

FIG. 2 is an enlarged sectional view taken on line 2—2 of the proximal end of the assembled applicator of FIG. 1 with a soft tampon.

FIG. 2A is similar to FIG. 2 with a highly compressed tampon.

FIG. 3 is an enlarged sectional view taken on line 3—3 of a potion of the proximal end of FIG. 2, showing position of a stiff cog at assembly.

FIG. 4 is an enlarged sectional view taken on line 4—4 of a portion of the proximal end of FIG. 2A.

FIG. 4A is similar to FIG. 4 showing another embodiment with the highly compressed tampon.

FIG. 5 is an enlarged sectional view showing another shape of the stiff cog in fabrication.

DESCRIPTION OF THE PREFERRED EMBODIMENTS

The preferred embodiments of the tampon applicator assembly incorporating the principles of this invention shown in FIGS. 1 to 5.

FIG. 1 illustrates the components of the assembly, namely a catamenial tampon 20, an inner tube 30, and an outer tube 50 in collapsed, prior-to-use position.

The assemblage and its components are shown with the proximal or front end on the readers left and the distal or rearward end on the readers right.

As shown in FIG. 1 the tampon 20 has mostly cylindrical configuration with a slightly rounded proximal end 21 for easier insertion. From a rear edge 22 of tampon 20 extends a cord 23 for withdrawal of used tampon 20 from vagina. A small portion 24 of tampon 20 protruding from a proximal end 31 of inner tube 30 and the remaining portion 25 storing therein.

The inner tube 30 is generally cylindrical thin-walled tube comprising at a distal end 32 a flange 33 and at proximal end 31 provided with a set of radially inwardly biased short fingers 34 divided by slots 35.

In fabrication diameter of the inscribed circle through free ends of fingers 34 is smaller than outside diameter of tampon 20 and when inner tube 30 and tampon 20 assembled together those diameters are equal.

On the outer surface of the inner tube 30 adjacent to fingers 34 there is a circumferential projection 36.

The outer tube 50 is generally cylindrical thin-walled tube or slightly tapered to satisfy requirements of molding technology.

At a distal end 51 outer tube 50 comprises a flange 52 on the outer surface and a circumferential projection 53 on the inner surface. The clear diameter of projection 53 is smaller than the maximum diameter of projection 36 on the inner tube 30.

A proximal discharge end 54 of outer tube 50 is closed by a set of radially inwardly biased petals 55 divided by slots 56.

As shown in FIGS. 1, 2 and 2A, on the inner surface of outer tube 50 adjacent to the bases of petals 55 there is a set of stiff cogs 57 circumferentially extended and fixed thereto.

Each cog 57 has the form of a truncated irregular pyramid canted toward the proximal discharge end 54. A proximally faced surface 58 of cog 57 inclined to the axis of outer tube 50 approximately from 70° to 85°.

A truncating surface 59 has concave configuration in the circumferential direction and is inclined to the axis of outer tube 50 approximately from 5° to 25°. The bigger figures of this limit are preferred for tampons 20 fabricated relatively soft (shown in FIG. 3) and the smaller figures for highly compressed tampons 20 (shown in FIG. 4).

Each cog 57 fixed to the inner surface of outer tube 50 by a base 60. A distant end 61 of cog 57 has tapered configuration confined by surfaces 58 and 59, crossing of which creates a curvilinear biting edge 62. The diameter of the inscribed circle through biting edges 62 is slightly smaller than the diameter of tampon 20.

The assembly process consists of several simple steps.

First step includes placing of proximal end 21 of tampon 20 behind distal end 32 of inner tube 30 in the longitudinally aligned position, whereat tampon 20 can be pushed through inner space of inner tube 30 until small portion 24 will protrude therefrom.

Second step includes placing of assembled in first step couple so that the protruding small portion 24 of tampon 20 will be located behind flange 52 of outer tube 50 in longitudinally aligned position.

Next step includes movement of this couple into outer tube 50 until proximal end 21 of tampon 20 will reach inner surfaces of petals 55.

Before the end of this movement, tampon 20 coacts with surfaces 59 of cogs 57 and moves the latter radially outwards until diameter of the inscribed circle through biting edge 62 will be equal to diameter of tampon 20. As soon as cogs 57 are moved outwards, sections 64 of the wall of outer tube 50 between cogs 57 become deformed.

The deformed section 64 keeping pressure on cogs 57 and, accordingly, biting edges 62 permanently forcibly contacted to the side surface of tampon 20. From the moment when tampon 20 contacts surfaces 59 up to the moment when edge 22 of tampon 20 passes biting edges 62 during the expelling of tampon 20, the set of cogs 57 functioning as tampon holding means.

As can be seen in FIG. 1 in completely assembled applicator, ends of fingers 34 located adjacent distally of cogs 57, thereby distal end 32 of inner tube 30 protrudes from distal end 51 of outer tube 50 so that the distance between flanges 33 and 52 slightly bigger than the distance between the ends of fingers 34 and the ends of petals 55. This is necessary to guarantee complete expelling of tampon 20 through proximal discharge end 54.

To prepare the applicator for use, a user has to withdraw inner tube 30 partially in the distal direction. By two fingers of one hand, the user has to hold distal end 51. By fingers of the other hand she has to grip distal end 32 and apply a distally directed longitudinal force. This force has to be sufficient to slide inner tube 30 over tampon 20.

The withdrawal of inner tube 30 has to be continued until projection 36 will stretch against projection 53.

During the withdrawal, cogs 57 with tapered ends pointed against direction of movement of inner tube 30, and biting edges 62, forcibly pressed against side surface of protruding portion 24 of tampon 20 by force created during assembly of the applicator by deforming of section 64, prevent distal movement of tampon 20.

Such arrangement of tampon holding means necessitated applying of a force several times bigger for movement of tampon 20 in distal direction than for movement of the latter in proximal direction.

When the applicator is prepared for use, the user inserts it into the body cavity and applies to the distal edge of inner tube 30 a proximally directed expelling force. This force is slightly bigger than the force that is necessary to apply to tampon 20 to move it through the tampon holding means, because it is necessary to apply an extra force to open and keep opened the petals 55.

When flange 33 stretches against flange 52, tampon 20 is completely expelled.

During assembly of the applicator, preparation for use, and expelling of tampon 20 three critical forces were used.

The first force is that, which is used in the first assembly step for pushing tampon 20 through inner space of inner tube 30 and it is equal to a force which is necessary to apply to inner tube 30 for sliding the latter over tampon 20 during partial withdrawal of inner tube 30. This force can be considered as sufficient if it is equal to a few tens of grams. Such force can be reached by choosing proper tightness of interference fit between tampon 20 and inner surface of inner tube 30.

Advantage of using such small force is more understandable in comparison with a force for identical purpose in prior art.

For instance, an applicator described in U.S. Pat. No. 4,846,802 has a tampon with an enlarged head. For entering of this head into the inner tube is necessary to apply longitudinal force up to 1000 grams and often even more. Sometimes the tampon snatches the inner tube out of a tube holding device, that causes jams. Result of such events is losses of material, losses of machinery time, and, accordingly, decrease of production and increased cost of manufacturing.

The second force is a longitudinal force applied to tampon 20 to activate the proximal movement of the latter through the tampon holding means.

The third force is a tampon holding force. The maximum holding force is equal to the longitudinal force, which is necessary to apply to tampon 20 to move the latter in the distal direction. The exact value of the second and the third forces, being in straight proportion, can be changed in equal degree by changing some parameters of the tampon holding means. Those parameters include amount of cogs 57; extension of biting edge 62 from inner surface of outer tube 50, i.e. changing diameter of inscribed circle through biting edges 62; circumferential length of base 60 of each cog 57.

Besides, there are parameters, changing of which allows to change the value of the second force without changing the value of the third force and vice versa.

By changing the angle between truncating surface 59 and axis of the outer tube 50, the value of the second force can be changed. The configuration of truncating surface 59 can also be changed as shown in FIG. 5. This is a convexo-concave configuration (convex in longitudinal direction and concave circumferentially) allowing to reduce the angle between truncating surface 59 and axis of outer tube 50 to less than By changing the angle between proximally faced surface 58 and the axis of outer tube 50 the value of the third force can be changed. As shown in FIG.4A, the third force can be increased without a significant increase of the second force by providing of each cog 57 with two biting edges 62 and 62', created by two truncating surfaces 59 and 59' with a step 63 therebetween.

By changing one or more parameters described above, a predetermined relation between all three forces can be reached, but in any case, overall dimensions of each cog 57 have to be greater than the thickness of the wall of outer tube 50 at location of the tampon holding means to keep sufficient stiffness of cogs 57.

A different principle of holding appears if tampon 20 is relatively soft (as shown in FIG. 3). In this case, tapered ends 61 of cogs 57 penetrate into tampon 20 under pressure of deformed sections 64. The process of penetration continues during the period of time between assembly of the applicator and its use. Although radially directed pressure decreased, the tampon holding effect is sufficient, because ends 61 of cogs 57 became a positive support against movement of tampon 20 in the distal direction.

Although the present invention has been described in relation to particular embodiments thereof, many other variations and modifications will become apparent to those skilled in the art.

Different amount of cogs 57 can be used in one set, also more than one set of cogs 57 can be provided. For instance, if in the set comprising six cogs 57 (shown in FIG. 2 and FIG. 2A) each second cog 57 will be slightly displaced in the distal direction, the tampon holding means will comprise two sets of cogs 57 with three of them in each set. This will lead to more gradual change of the values of forces, i.e. smoother assembly and operation during the expelling of tampon 20.

Inner tube 30 and outer tube 50 may be constructed of materials, physical and chemical properties of which are suitable for this kind of product and manufacturing processes.

It is preferred therefore, that the present invention be limited not by specific disclosure herein, but by the scope of the appended claims.

I claim:

1. A compactly assembled tampon applicator comprising:
    a tampon shaped for intra-vaginal insertion having any configuration, acceptable for the projected function, including straight cylindrical configuration;
    an inner tube including a proximal end adapted to store said tampon fitted therein with a relatively small portion of said tampon protruding therefrom;
    an outer tube telescopically fitted over said inner tube and having a proximal discharge end;
    a stopping means to prevent complete withdrawal of said inner tube from said outer tube during preparation of the applicator for use;
    a holding means to prevent distal movement of said tampon relative to said outer tube during partial distal withdrawal of said inner tube over said tampon; wherein said holding means comprises at least one set of circumferentially extended stiff cogs, each of which comprises a base, by which said stiff cog is rigidly fixed to an acting portion of said outer tube at a location of said protruding portion of said tampon, and, on the opposite side from said base, at least one biting edge defined by the crossing of a proximally faced surface and a truncating surface, said acting portion of said outer tube in vicinity of said base comprises flexible sections having a predetermined flexibility, so that in the assembled applicator said stiff cogs are radially outwardly displaced by said protruding portion of said tampon and said flexible sections are deformed and stressed, whereby said flexible sections being in the deformed and stressed condition create radially inwardly directed forces allowing to keep said biting edges constantly contacted with sufficient forces to the side surface of said protruding portion of said tampon.

2. The applicator of claim 1 wherein each said cog is fabricated as a truncated irregular pyramid canted toward said proximal discharge end, so that said biting edge is positioned proximally relative to said base and has a curvilinear configuration firmly grasping said tampon.

3. The applicator of claim 2 wherein in fabrication the diameter of an inscribed circle through said biting edges is smaller than the diameter of said tampon.

4. The applicator of claim 3 wherein said truncating surface is inclined at a substantially small angle to the axis of said outer tube allowing passage of said tampon in the proximal direction by applying a longitudinal force smaller than the acceptable tampon expelling force and said proximally faced surface is inclined to said axis at an angle slightly less than 90 degrees allowing effective increase in tampon holding force during the partial withdrawal of said inner tube.

5. The applicator of claim 4 wherein each said stiff cog has the overall dimensions significantly exceeding the thickness of said flexible sections assuring sufficient stiffness of said stiff cogs and flexibility of said flexible sections for proper function under the action of operating forces.

6. The applicator of claim 5 wherein said tubes are made of molded plastic, having a stiffness of from 10,000 to 90,000 psi.

7. A compactly assembled tampon applicator comprising:
    a tampon shaped for intravaginal insertion having any configuration, acceptable for the projected function including straight cylindrical configuration:
    an inner tube including a proximal end adapted to store said tampon fitted therein with a relatively small portion of said tampon protruding therefrom;
    an outer tube telescopically fitted over said inner tube and having a proximal discharge end;
    a stopping means to prevent complete withdrawal of said inner tube from said outer tube during preparation of the applicator for use;
    a holding means to prevent distal movement of said tampon relative to said outer tube during partial distal withdrawal of said inner tube over said tampon; wherein
    said holding means comprises an acting portion of said outer tube, having a predetermined thickness to assure a desired flexibility of said acting portion, and a set of circumferintially extended stiff cogs, each said stiff cog having a base, a proximally faced surface, a truncating surface and a biting edge as a result of the crossing of said proximally faced surface and said truncating surface, said base rigidly fixed to said acting portion of said outer tube and said biting edge engaged with the side surface of said protruding portion of said tampon so that in the assembled applicator each said stiff cog is displaced radially outwardly by said tampon and sections of said acting portion in the vicinity of said bases are in a deformed and stressed state creating radially inwardly directed forces to assure forcible engagement of said biting edges with the side surface of said tampon.

8. The applicator of claim 7 wherein said protruding portion of said tampon comprises an enlarged in diameter head positioned proximally of said stiff cogs allowing to reduce the tampon expelling force and to keep said sections of said acting portion in the deformed and stressed state only during the assemblage of the applicator.

9. The applicator of claim 7 wherein each said stiff cog has the overall dimensions significantly exceeding the thickness of said sections of said acting portion assuring sufficient stiffness of said stiff cogs and flexibility of said sections under the action of existing functioning forces during the assemblage, preparation for use and use of the applicator.

10. The applicator of claim 7 wherein each said cog is fabricated as a truncated irregular pyramid canted toward said proximal discharge end, so that said biting edge is positioned proximally relative to said base and has a curvilinear configuration firmly grasping said tampon.

11. The applicator of claim 7 wherein, in fabrication, a diameter of the inscribed circle through said biting edges is smaller than the diameter of said tampon.

12. The applicator of claim 7 wherein said truncating surface is inclined at a substantially small angle to the axis of said outer tube allowing passage of said tampon in the proximal direction by applying a longitudinal force smaller than the tampon expelling force and said proximally faced surface is inclined to said axis at an angle slightly less than 90 degrees allowing effectively in increase a tampon holding force during partial withdrawal of said inner tube.

* * * * *